(12) United States Patent
Pak

(10) Patent No.: US 8,527,365 B2
(45) Date of Patent: Sep. 3, 2013

(54) METHOD FOR PROVIDING CUSTOMIZED COSMETICS AND THE SYSTEM USED THEREFOR

(75) Inventor: Dong Sun Pak, Yongin-si (KR)

(73) Assignee: Aram Huvis Co., Ltd., Seongnam-si (KR)

( * ) Notice: Subject to any disclaimer, the term of this patent is extended or adjusted under 35 U.S.C. 154(b) by 275 days.

(21) Appl. No.: 12/281,843

(22) PCT Filed: Sep. 7, 2007

(86) PCT No.: PCT/KR2007/004337
§ 371 (c)(1),
(2), (4) Date: Sep. 5, 2008

(87) PCT Pub. No.: WO2008/035877
PCT Pub. Date: Mar. 27, 2008

(65) Prior Publication Data
US 2009/0076639 A1 Mar. 19, 2009

(30) Foreign Application Priority Data
Sep. 18, 2006 (KR) .................. 10-2006-0089974

(51) Int. Cl.
G06Q 30/00 (2012.01)
G06G 1/14 (2006.01)
G06Q 20/00 (2012.01)
G06Q 10/00 (2012.01)

(52) U.S. Cl.
USPC ............. 705/26.5; 705/22; 705/26.7; 705/28

(58) Field of Classification Search
USPC ........................................... 705/26
See application file for complete search history.

(56) References Cited

U.S. PATENT DOCUMENTS

| 5,972,322 | A * | 10/1999 | Rath et al. ............ 424/70.11 |
| 5,993,792 | A * | 11/1999 | Rath et al. ............ 424/70.28 |
| 6,598,627 | B2 * | 7/2003 | Manzari et al. .......... 141/104 |
| 6,672,341 | B2 * | 1/2004 | Bartholomew et al. ..... 141/18 |
| 7,349,857 | B2 * | 3/2008 | Manzo ...................... 705/2 |
| 2003/0064356 | A1 * | 4/2003 | Rubinstenn et al. ...... 434/377 |
| 2004/0218099 | A1 * | 11/2004 | Washington ............. 348/571 |
| 2005/0240085 | A1 * | 10/2005 | Knoell et al. ............ 600/300 |

FOREIGN PATENT DOCUMENTS

| KR | 20010067927 A | 7/2001 |
| KR | 20030065181 A | 8/2003 |
| KR | 100708319 B1 | 4/2007 |
| WO | 01/91600 A2 | 12/2001 |
| WO | 02/082350 A1 | 10/2002 |

* cited by examiner

Primary Examiner — Ig T An
(74) Attorney, Agent, or Firm — Christensen O'Connor Johnson Kindness PLLC

(57) ABSTRACT

The present invention relates to a method and system for providing cosmetics customized for an individual customer, and more particularly, to a method and system for providing cosmetics customized for an individual customer, wherein customized cosmetics appropriate for skin condition or scalp and hair condition of the customer are produced using diagnostic data on the skin condition or scalp and hair condition of the customer and provided to the customer to thereby enhance customer's feeling of satisfaction. According to the present invention, there is provided a method for providing customized cosmetics appropriate for an individual customer using a microprocessor having information on standard cosmetic material mixing ratios in accordance with age groups and skin conditions of consumers as a database.

5 Claims, 5 Drawing Sheets

METHOD FOR PROVIDING CUSTOMIZED COSMETICS AND THE SYSTEM USED THEREFOR

This application is the U.S. National Phase entry under 35 U.S.C. §371 and claims the benefit of International Application No. PCT/KR2007/004337, filed Sep. 7, 2007, the entire contents of which are hereby incorporated herein by reference.

TECHNICAL FIELD

The present invention relates to a method and system for providing cosmetics customized for an individual customer, and more particularly, to a method and system for providing cosmetics customized for an individual customer, wherein customized cosmetics appropriate for skin condition or scalp and hair condition of the customer are produced using diagnostic data on the skin condition or scalp and hair condition of the customer and provided to the customer to thereby enhance customer's feeling of satisfaction.

BACKGROUND ART

Generally, cosmetics are classified and massively manufactured according to several skin types and provided to consumers. Such cosmetics should not cause troubles to all or majority of people, rather than satisfying requirements of numerous types of customers. However, although the consumers request cosmetics most appropriate for their own skin conditions, cosmetics manufactured not to bring troubles to majority of people are very unlikely to be appropriate for likings or skin condition of a specific consumer.

In addition, the cosmetics massively manufactured as described above tend to be easily overstocked due to characteristics of mass productions, and increase in manufacturing costs brought by overstock will entirely remains as consumers' burdens.

In the meantime, women in the present days increasingly participate in social activities and gain economical stabilities, and thus, do not hesitate to invest in the women themselves. Cosmetics can be an example of the investments, and the women purchase expensive name-brand cosmetics without hesitation. However, there is a problem in that even the expensive name-brand cosmetics are also no more than massively produced cosmetics and not the cosmetics that are customized appropriately for skin condition of individual consumers, and prices are determined almost by brand names, so that the prices of such cosmetics are too high as compared with effectiveness of the cosmetics.

Therefore, requested is a service that can minimize distribution channels of customized cosmetics appropriate for likings and skin conditions of individual consumers in order to provide the cosmetics to consumers in a shortest time from a manufacturing point at a relatively low price.

DISCLOSURE OF INVENTION

Technical Problem

The present invention is conceived to solve the aforementioned problems. An object of the present invention is to provide a method and system for providing cosmetics customized for an individual customer, in which skin condition or scalp and hair condition of the customer is measured using a diagnosis device, a cosmetic material mixing ratio appropriate for the customer is calculated on the basis of information on the measured skin condition or scalp and hair condition of the customer, optimally customized cosmetics are manufactured using the calculated cosmetic material mixing ratio, for which composition ratio of materials used for the cosmetics is appropriately adjusted in accordance with the skin condition or scalp and hair condition of the customer, and the customer is provided with the manufactured cosmetics, whereby it is possible to maximally fulfill demands of the customer who desires cosmetics perfectly appropriate for himself or herself.

Technical Solution

According to the present invention for achieving the objects, there is provided a method for providing customized cosmetics appropriate for an individual customer using a microprocessor having information on standard cosmetic material mixing ratios in accordance with age groups and skin conditions of consumers as a database. The method comprises the steps of measuring skin condition of a customer using a diagnosis device; calculating a cosmetic material mixing ratio appropriate for the customer through the microprocessor on the basis of information on the measured skin condition of the customer by adding or subtracting a mixing ratio of materials that need to be adjusted depending on the skin condition to or from a standard cosmetic material mixing ratio previously stored in the microprocessor in accordance with an age group and skin condition; and manufacturing the customized cosmetics using the calculated cosmetic material mixing ratio and providing the customer with the manufactured cosmetics.

In addition, according to the present invention for achieving the object, there is provided a system for providing customized cosmetics appropriate for an individual customer using a microprocessor having information on standard cosmetic material mixing ratios in accordance with age groups and skin conditions of consumers as a database. The system comprises a diagnosis device for measuring skin condition of a customer; the microprocessor receiving information on the skin condition measured by the diagnosis device and calculating a cosmetic material mixing ratio appropriate for the customer on the basis of the received information on the skin condition of the customer by adding or subtracting a mixing ratio of materials that need to be adjusted depending on the skin condition to or from a standard cosmetic material mixing ratio previously stored in the microprocessor in accordance with an age group and skin condition; and a cosmetic manufacturing apparatus for receiving the cosmetic material mixing ratio from the microprocessor and manufacturing the customized cosmetics.

Advantageous Effects

The method and system for providing cosmetics customized for an individual customer according to the present invention provides the customer with customized cosmetics manufactured by calculating an optimal cosmetic material mixing ratio appropriate for skin condition or scalp and hair condition of the customer to thereby fulfill customer's satisfaction, and furthermore, cosmetic samples are manufactured and provided to the customer before the customized cosmetics are provided to the customer to thereby effectively maximizing customer's satisfaction.

Furthermore, the present invention provides a system able to be exported in a turnkey base including a technique of measuring skin condition or scalp and hair condition, prescriptions relevant to the measured skin condition or scalp and hair condition, accumulated clinic test data, and facilities for manufacturing customized cosmetics.

Figure 1:
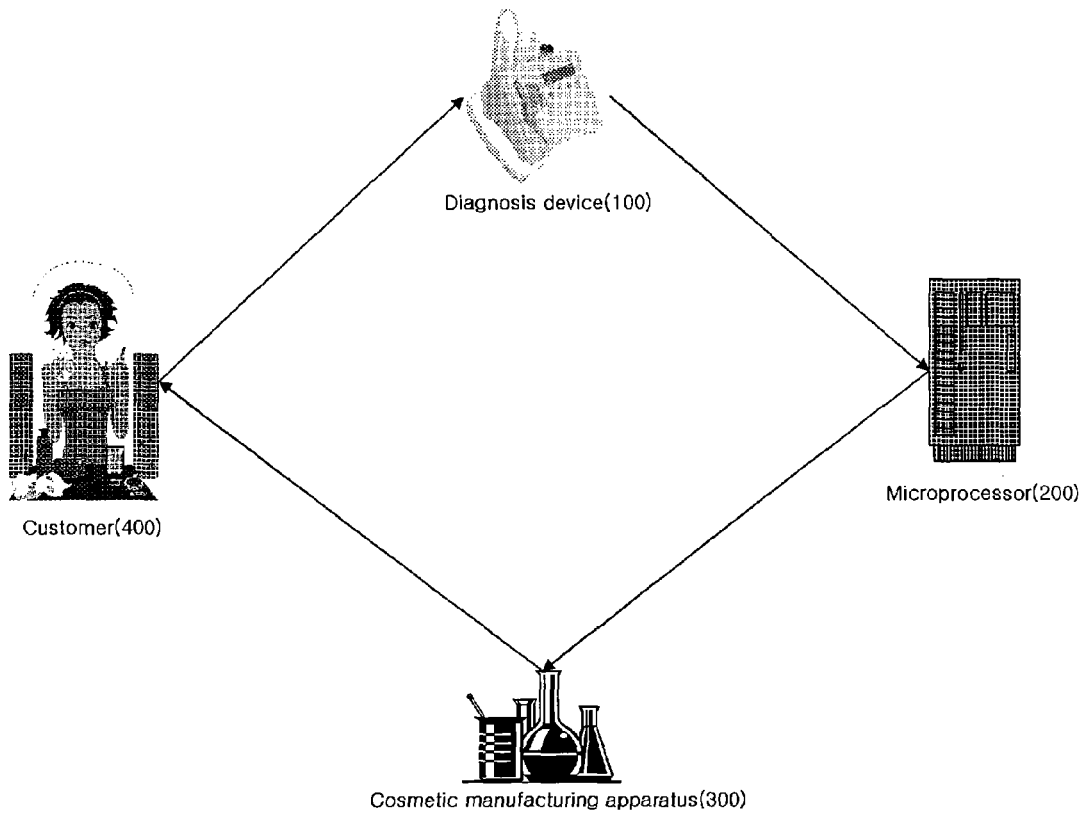
FIG. 1 is a view showing a conceptual configuration of a system for providing cosmetics customized for an individual customer according to the present invention.

EXPLANATION OF REFERENCE NUMERALS
FOR MAJOR PORTIONS SHOWN IN
DRAWINGS

100: Diagnosis device
200: Microprocessor
300: Cosmetic manufacturing apparatus
400: Customer

BEST MODE FOR CARRYING OUT THE
INVENTION

Hereinafter, a preferred embodiment of the present invention will be described in detail with reference to the accompanying drawings.

Figure 2:
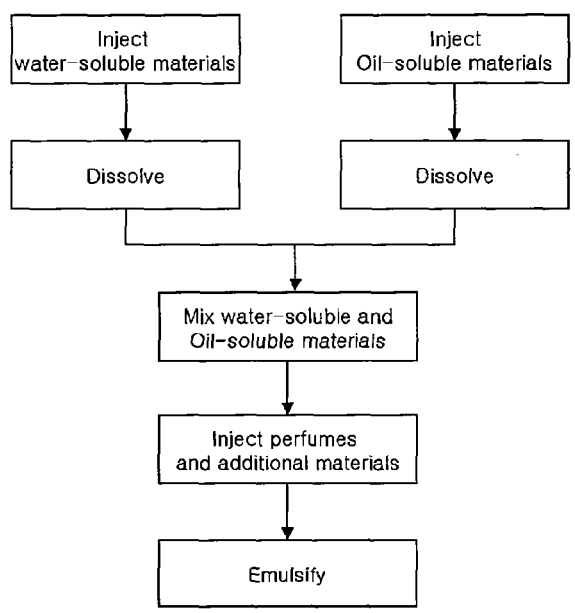
FIG. 2 is a flowchart illustrating a process of manufacturing customized cosmetics by a cosmetic manufacturing apparatus in the system for providing cosmetics customized for an individual customer according to the present invention.

FIG. 1 is a view showing a conceptual configuration of a system for providing cosmetics customized for an individual customer according to the present invention, and FIG. 2 is a flowchart illustrating a process of manufacturing customized cosmetics by a cosmetic manufacturing apparatus in the system for providing cosmetics customized for an individual customer according to the present invention.

Referring to FIG. 1, a system for providing cosmetics customized for an individual customer comprises a diagnosis device 100 for measuring skin condition or scalp and hair condition of a customer 400, a microprocessor 200 for receiving information on the skin condition or scalp and hair condition of the customer 400 from the diagnosis device 100 and calculating a cosmetic material mixing ratio appropriate for the customer using the received information, and a cosmetic manufacturing apparatus 300 for receiving the cosmetic material mixing ratio from the microprocessor 200 and manufacturing cosmetic samples and customized cosmetics to be provided to the customer 400.

Various forms of devices can be used as the diagnosis device 100 for measuring skin condition or scalp and hair condition of the customer 400. For example, it is possible to use a device such as "skin diagnose system" of Korean Patent No. 609823 (registration date: Jul. 31, 2006) applied and registered in the name of the present applicant. The diagnosis device 100 can be used for measuring scalp and hair condition of the customer 400 as well as skin condition of the customer, wherein a lens used for measuring scalp and hair condition has a higher magnifying power than a lens used for generally measuring skin condition.

The configuration and operation of the diagnosis device 100 will be briefly described. The diagnosis device 100, which is a means for collecting information on skin condition or scalp and hair condition, has a first camera for taking photographs of a pore distribution diagram, pore size, pigmentation, and keratin and other atopy of skin and obtaining picture image information thereon, or taking photographs of scalp condition, the number of hairs, hair thickness, hair condition, pore condition, and hair loss state and obtaining picture image information thereon. Any one of lenses L, L1, L2 and L3 having different magnifications can be selected and coupled to the first camera as needed. The type of the lens that can be coupled to the first camera includes X1, X60, X200, and X1000 magnification lenses. For example, the X1 and X60 lenses are used to measure skin condition of the customer 400, while the X1, X60, X200, and X1000 magnification lenses are used to measure scalp and hair condition.

The diagnosis device further comprises a moisture measuring unit for obtaining a moisture distribution ratio of skin through direct contact with the skin and processing numeric values, an elasticity measuring stick having a solenoid valve, a vacuum pump and a motor drive unit to measure elasticity of the skin and determine aging of the skin, a sebum measuring stick for collecting sebum of the skin through a sebum tab and inputting picture image information on the sebum into a second camera, and a keratin measuring stick for collecting keratin through a keratin tab and inputting picture image information on the keratin into the second camera.

In addition, the diagnosis device comprises a central processing unit for controlling and transmitting information input from the first camera, the moisture measuring unit, the elasticity measuring stick, the sebum measuring stick, and the keratin measuring stick, which are means for collecting information on skin or scalp and hair, an interface unit for transmitting image signals (pore, pigmentation, sebum, keratin, scalp condition, hair condition, pore condition, the number of hairs, hair thickness, and hair loss state) and numeric signals (elasticity and moisture) of the central processing unit to a computer or transmitting the image and numeric signals that are image-analyzed and processed by the computer to the central processing unit again, and an LCD unit for outputting information obtained from a means for collecting information on skin or scalp and hair in numerical values via the central processing unit.

Through the diagnosis device 100 configured as described above, it is possible to correctly measure information on customer's skin, i.e., integrated information mainly on a face, such as a pore distribution diagram, pore size, pigmentation, keratin and other atopy, moisture, elasticity, sebum, keratin, scalp condition that is integrated information on scalp and hair, the number of hairs, hair thickness, hair condition, pore condition, and hair loss state.

The diagnosis device 100 can be personally possessed by a customer or can be installed in a sales office where customized cosmetics are sold, hospital, or the like. The diagnosis device 100 is connected to a user personal computer (PC) that is connected to a network, so that information on the measured skin condition or scalp and hair condition can be stored in the user PC or transmitted to the microprocessor through the network.

The microprocessor 200 receives the information on the skin or scalp and hair measured by the diagnosis device 100, calculates a cosmetic material mixing ratio appropriate for the skin or scalp and hair of the customer, and transmits the calculated cosmetic material mixing ratio to the cosmetic manufacturing apparatus 300.

The cosmetic manufacturing apparatus 300 manufactures cosmetic samples or customized cosmetics appropriate for the skin or scalp and hair of the customer using the cosmetic material mixing ratio received from the microprocessor 200.

The cosmetic manufacturing apparatus 300 of the present invention comprises a first processing line for dissolving water-soluble materials, a second processing line for dissolving oil-soluble materials, and a mixed processing line for mixing the dissolved water-soluble and oil-soluble materials, injecting perfumes and additional materials thereinto, and emulsifying the mixed materials.

Referring to FIG. 2, cosmetic materials are divided into water-soluble materials and oil-soluble materials, and since there are a lot of difficulties in mixing a variety of water-soluble and oil-soluble materials at the same time, the water-soluble materials and oil-soluble materials are dissolved in different processing lines.

In the processing line for dissolving water-soluble materials, a variety of water-soluble materials are injected into a water-soluble material mixing container at a pre-determined mixing ratio. Then, the container is mounted to a dissolving device, and the injected water-soluble materials are dissolved to be uniformly mixed.

In the same manner, in the processing line for dissolving oil-soluble materials, a variety of oil-soluble materials are injected into an oil-soluble material mixing container at a predetermined mixing ratio. Then, the container is mounted to a dissolving device, and the injected oil-soluble materials are dissolved to be uniformly mixed.

Thereafter, the dissolved water-soluble and oil-soluble materials are mixed in a cosmetic mixing container, and perfumes and additional materials are injected thereinto. Then, customized cosmetics in an emulsified state are manufactured by emulsifying the materials in the mixing container.

Hereinafter, a method for providing cosmetics customized for an individual customer according to the present invention will be described.

Figure 3:
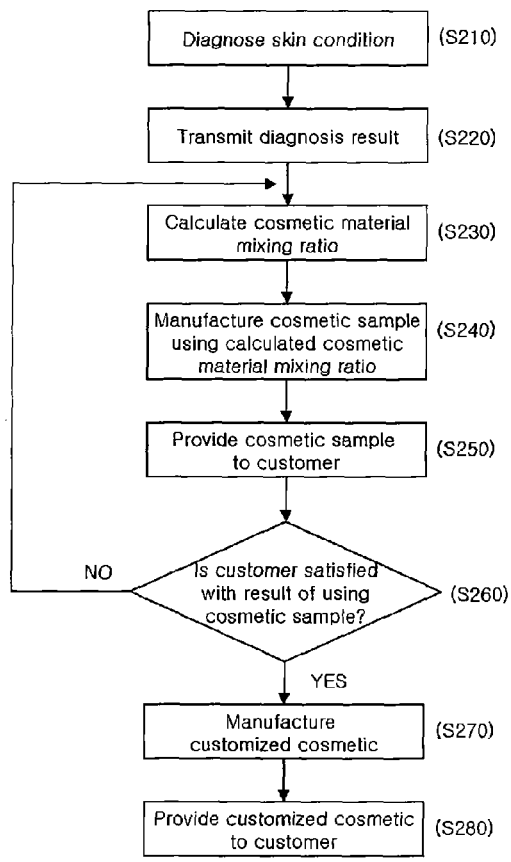
FIG. 3 is a flowchart sequentially illustrating a process of providing customized cosmetics to a customer through a method of providing cosmetics customized for an individual customer according to the present invention.
Figure 4:
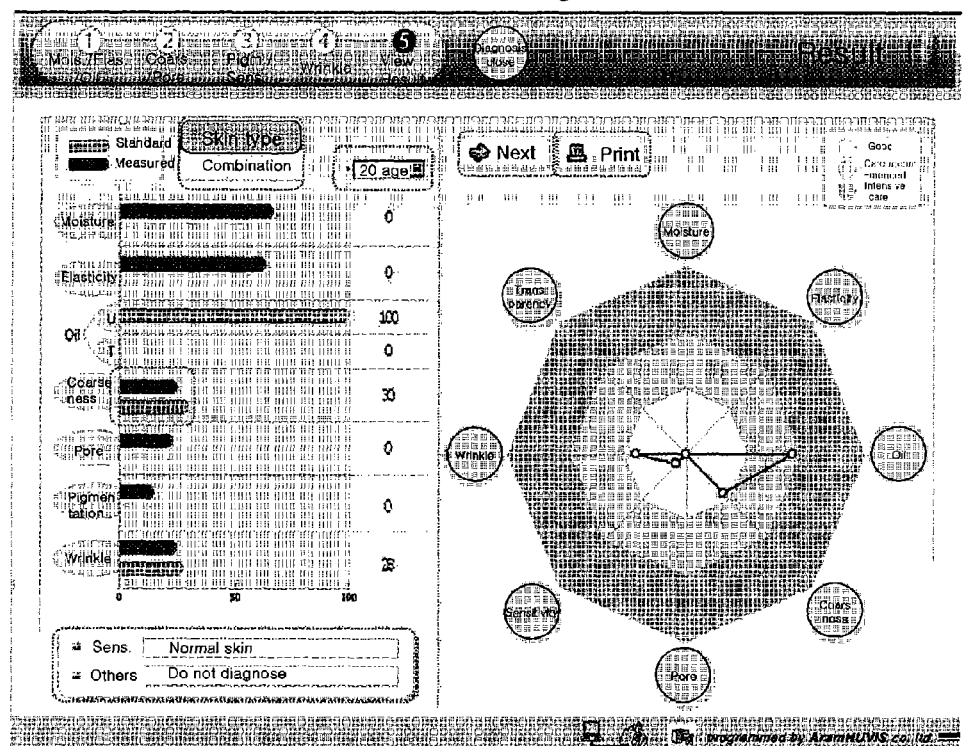
FIGS. 4 to 6 are monitor screens showing a result of analyzing skin condition in the method of providing cosmetics customized for an individual customer according to the present invention.
Figure 5:
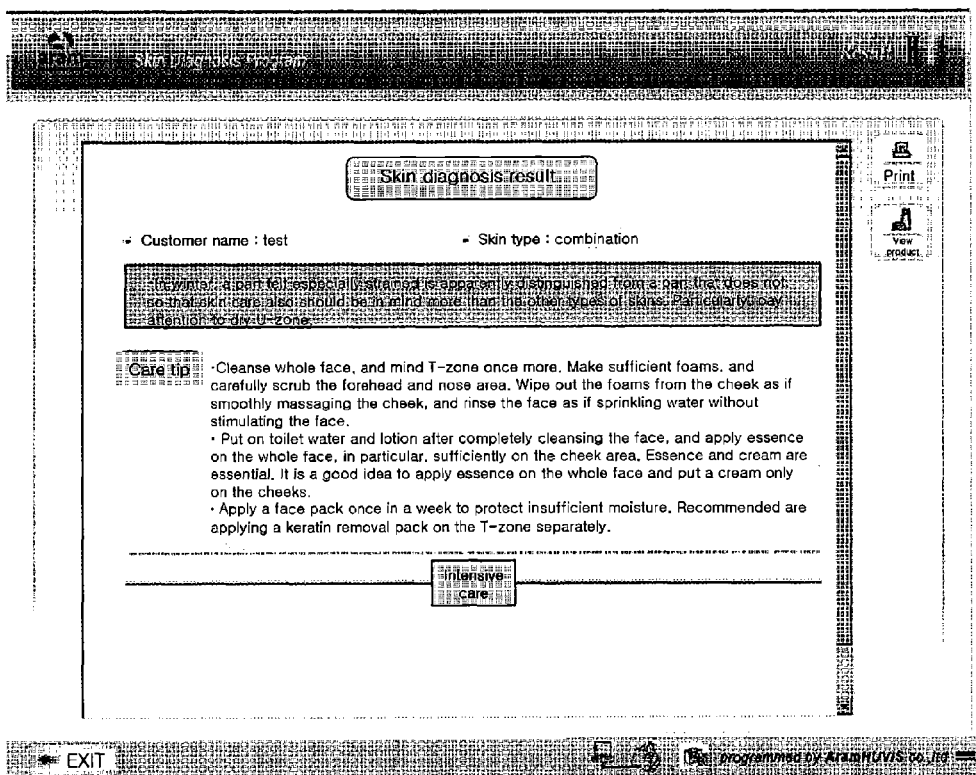
Figure 6:
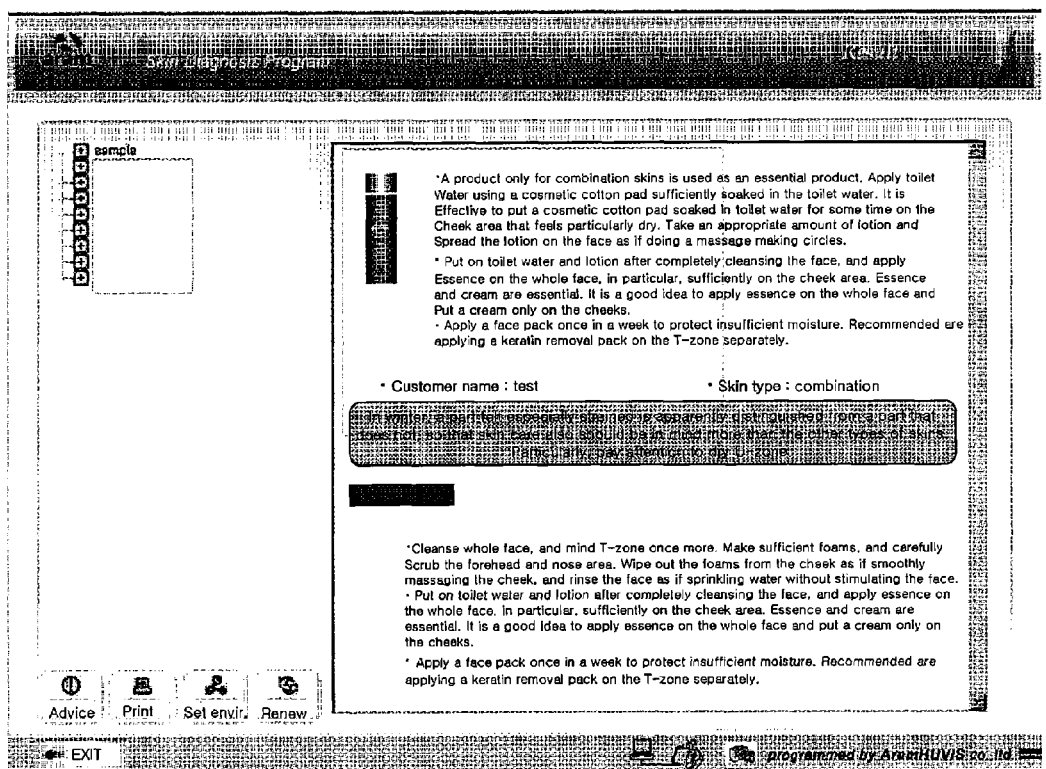
Figure 7:
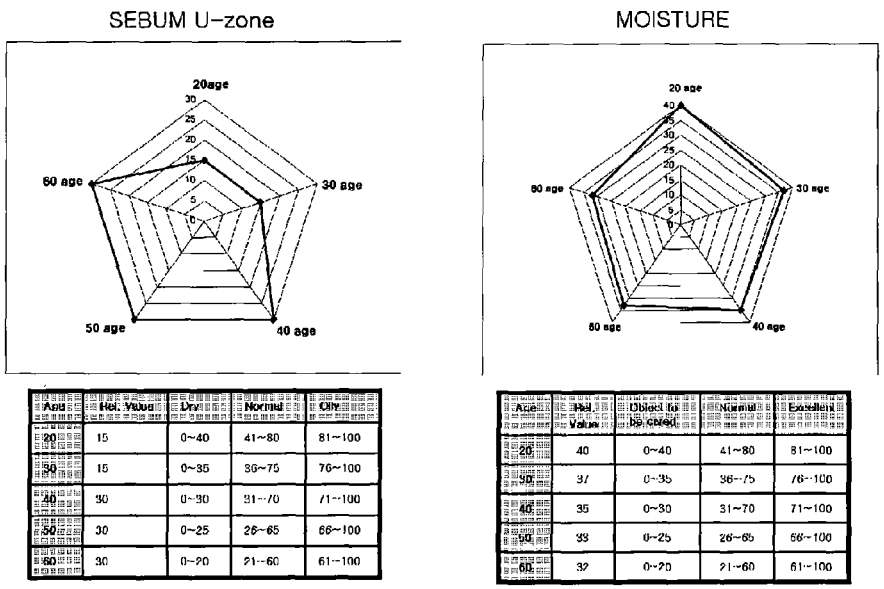
FIG. 7 is a table and graph expressing skin condition of each age group in numerical data converted in percentages.

FIG. 3 is a flowchart sequentially illustrating a process of providing customized cosmetics to a customer through a method of providing cosmetics customized for an individual customer according to the present invention. In addition, FIGS. 4 to 6 are monitor screens showing a result of analyzing skin condition in the method of providing cosmetics customized for an individual customer according to the present invention, and FIG. 7 is a table and graph expressing skin condition of each age group in numerical data converted in percentages. The figures will be described in association with one another.

First, skin condition of a customer is measured through the diagnosis device that measures skin condition (step S210). This measuring step may be performed by a customer at home using a purchased or leased diagnosis device to measure condition of his or her skin or may be performed at a cosmetics store or hospital where a diagnosis device is installed. A measurer (or customer) inputs sex, age, and the like of the customer referring to the manual before measuring skin condition. Then, the measurer (or customer) measures skin condition in order of moisture, elasticity, sebum, skin texture (coarseness), pore size, pigmentation, sensitivity, and wrinkles referring to the manual of the diagnosis device.

In the meantime, an additional step of diagnosing by interview can be included in this step. If the diagnosis by interview is utilized, it can be helpful to measure the skin condition of the customer through the customer's living environment, dietary habits, and the like.

The diagnosis device informs the customer of a result of an analysis performed on the skin condition by itself through a PC monitor connected to the diagnosis device. As shown in FIGS. 4 to 6, the diagnosis device gives information on skin type of the customer and a part of the skin that needs a special care, together with a result of the measurement performed on each part of the skin of the customer, in addition to skin care tips.

The skin type of the customer shown in FIGS. 4 to 6 is a combination skin, which shows that the skin needs a care for skin sebum, and particularly, the U-zone is very dry. A graph of FIG. 4 shows the parts that need further intensive care from the center toward outside and shows that sebum needs to be cared among the diagnosed items. FIGS. 5 and 6 give information on skin care tips, particularly intensive care tips about the U-zone of the face.

The skin care tips shown in FIGS. 5 and 6 are prepared on the basis of the data shown in FIG. 7. Although FIG. 7 shows values only about sebum and moisture, numerical data on skin texture, elasticity, pore size, skin texture, pigmentation, sensitivity, and wrinkles are also previously stored. Such data includes standard values, numerical values that need to be cared, and normal values of each age group calculated from a result of a number of clinic tests. This proves that the skin care tips and the cosmetic material mixing ratio calculated after the skin condition is diagnosed are scientific.

Next, the information on the skin of the customer obtained by diagnosing the skin condition of the customer is transmitted to the microprocessor (step S220). The information on the skin of the customer is stored in the user PC connected to the diagnosis device and can be transmitted to the microprocessor through a wired or wireless communication network, such as the Internet or a plain network.

Then, the microprocessor analyzes the skin condition of the customer and calculates a cosmetic material mixing ratio appropriate for the skin condition of the customer on the basis of the previously stored data (step S230). Since a standard cosmetic material mixing ratio is previously set in the microprocessor in accordance with an age group and skin condition of a consumer, if the skin condition of the customer is analyzed, a cosmetic material mixing ratio appropriate for the skin condition of the customer can be calculated by adding or subtracting materials that need to be adjusted depending on the skin condition, through a comparison with the stored standard cosmetic material mixing ratio considering the age and skin condition of the consumer.

Tables 1 and 2 show material content ratios of a cream among various kinds of cosmetics as an example. Table 1 shows a content ratio appropriate for ordinary skins, and Table 2 shows a content ratio appropriate for nearly oily skins. The 'Part' shown in the tables represents a type of a material, wherein A and B are water-soluble materials, C is an oil-soluble material, D is a thickener, and E and F are additives.

TABLE 1

| Part | No. | Material name | Contents (%) |
|---|---|---|---|
| A | 1 | D Water | 71.580 |
|  | 2 | Nipagin M | 0.200 |
|  | 3 | Germall 115 | 0.200 |
| B | 4 | Glycerin | 6.000 |
|  | 5 | PG | 4.000 |
|  | 6 | Keltrol F | 0.100 |
| C | 7 | Glucate SS | 1.000 |
|  | 8 | Kalkol 6870 | 2.500 |
|  | 9 | GMS 105 | 1.000 |
|  | 10 | Arlacel 165 | 1.500 |
|  | 11 | Nipasol M (Danisol P) | 0.100 |
|  | 12 | Macadamia nut oil | 3.000 |
|  | 13 | LP-70 | 5.000 |
| D | 14 | Sepigel 305 | 1.600 |
| E | 15 | Pf | 0.050 |
| F | 16 | Sodium Hyaluronate 1% | 1.000 |
|  |  | Total | 98.830 |

TABLE 2

| Part | No. | Material name | Contents (%) |
|---|---|---|---|
| A | 1 | D Water | 71.580 |
|  | 2 | Nipagin M | 0.200 |
|  | 3 | Germall 115 | 0.200 |
| B | 4 | Glycerin | 4.000 |
|  | 5 | PG | 2.500 |
|  | 6 | Keltrol F | 0.100 |
| C | 7 | Glucate SS | 1.000 |
|  | 8 | Kalkol 6870 | 2.500 |
|  | 9 | GMS 105 | 1.000 |
|  | 10 | Arlacel 165 | 1.500 |
|  | 11 | Nipasol M (Danisol P) | 0.100 |
|  | 12 | Macadamia nut oil | 1.500 |
|  | 13 | LP-70 | 2.000 |
| D | 14 | Sepigel 305 | 1.600 |
| E | 15 | Pf | 0.050 |
| F | 16 | Sodium Hyaluronate 1% | 1.000 |
|  |  | Total | 90.830 |

Comparing Tables 1 and 2 with each other, it can be understood that contents of Glycerin and PG among water-soluble materials are decreased from 6.000% and 4.000% to 4.000% and 2.500% respectively and contents of Macadamia nut oil and LP-7 among oil-soluble materials are decreased from 3.000% and 5.000% to 1.500% and 2.000% respectively. Accordingly, it will be understood that cosmetics appropriate for oily skins are manufactured if cosmetics are manufactured using the cosmetic material content ratio shown in Table 2, while cosmetics appropriate for dry skins are manufactured if the cosmetic materials decreased in Table 2 are increased by a certain amount from the contents shown in Table 1. On the basis of the information on the measured skin condition, if the skin condition of a customer is in between a normal skin and an oily skin, a material mixing ratio of customized cosmetics appropriate for the skin of the corresponding customer can be calculated by appropriately adding or subtracting the mixing ratio of those materials in accordance with skin features of the customer.

The cosmetic material mixing ratio calculated in the microprocessor as described above is transmitted to the cosmetic manufacturing apparatus, and then, cosmetic samples are produced (step S240). The cosmetic samples are manufactured as many as the customer can use for a few days and put into prepared cosmetic bowls.

The manufactured cosmetic samples are provided to the customer (step S250).

Thereafter, the customer provided with the cosmetic samples uses the cosmetic samples for a certain period, confirms whether the cosmetic samples are appropriate for his or her skin, and informs the cosmetic manufacturing company of the result of using the cosmetic samples (step S260).

If the customer is satisfied with the cosmetic samples, cosmetics are manufactured using the same cosmetic material mixing ratio as that of the cosmetic samples (step S270).

On the other hand, in a case where the customer is not satisfied with the cosmetic samples since the cosmetic samples make skin troubles or the customer does not like the fragrance, the cosmetic material mixing ratio is recalculated by finding out the source of the dissatisfaction (step S230).

If the cosmetic material mixing ratio is recalculated, cosmetic samples are remanufactured using the recalculated cosmetic material mixing ratio (step S240), and the remanufactured cosmetic samples are provided to the customer again (step S250).

The customer uses the cosmetic samples provided again and informs the cosmetic manufacturing company of the result of using the cosmetic samples (step S260). Here, if the customer is satisfied with the cosmetic samples, the cosmetic manufacturing company manufactures customized cosmetics using the recalculated cosmetic material mixing ratio (step S270). Otherwise, steps S230 to S260 can be repetitively performed several times. All the manufacturing processes of the customized cosmetics are provided through the Internet when the customized cosmetics are manufactured, and the customer can confirm the manufacturing processes, a delivery process, and the like in real-time if necessary. This process gives the customer reliance to use the customized cosmetics in confidence.

The cosmetics manufactured as described above can be provided to the customer by an employee of the manufacturing company, a home delivery company, or the like (step S280). When the cosmetic samples or the customized cosmetics are provided to the customer, skin care tips appropriate for the skin condition can be given in writing based on the result of the skin condition measurement as shown in FIGS. 5 and 6.

If the customer consumes all the cosmetics and reorders the cosmetics, the part where skin care is required may be improved due to the use of the customized cosmetics, and another part may need to be cared. Therefore, a series of the processes are performed again, and cosmetics appropriate for the skin condition are requested to be manufactured.

The method and system for manufacturing cosmetics customized for an individual customer according to the present invention can be applied to hair care cosmetics used for caring scalps and hairs, as well as to normal skin care cosmetics. In other word, depending on scalp and hair condition of a customer, a material mixing ratio appropriate for the scalp and hair condition is calculated, and thus customized hair care cosmetics, such as shampoos, essences, hair packs, hair lotions, and the like, appropriate for the features of an individual customer can be provided.

Hereinafter, a case where the present invention is applied to hair care cosmetics will be described in further detail.

In order to apply the present invention to hair care cosmetics used for caring scalps and hairs, scalp and hair condition of a customer should first be measured. A process of calculating a material mixing ratio of hair care cosmetics appropriate for the scalp and hair condition of the customer on the basis of the result of the measurement is the same as the process described above.

Figure 8:
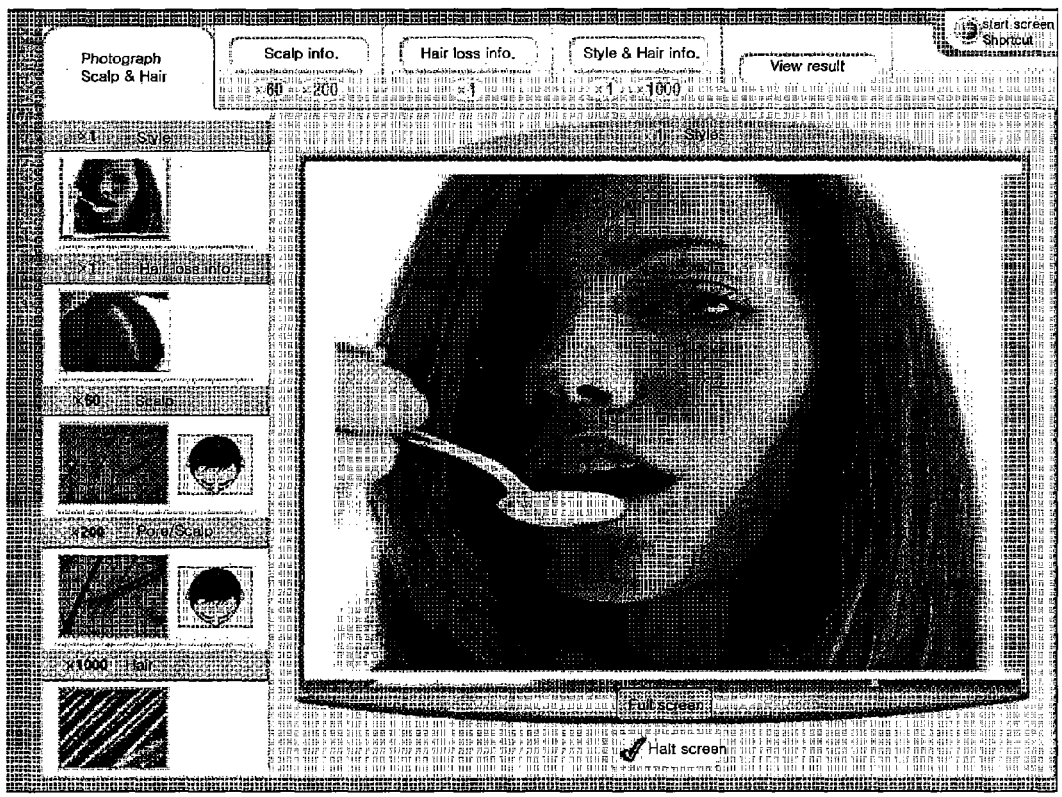
FIG. 8 is a monitor screen displaying picture images obtained by photographing scalp and hair of a customer in the method of providing cosmetics customized for an individual customer according to the present invention.
Figure 9:
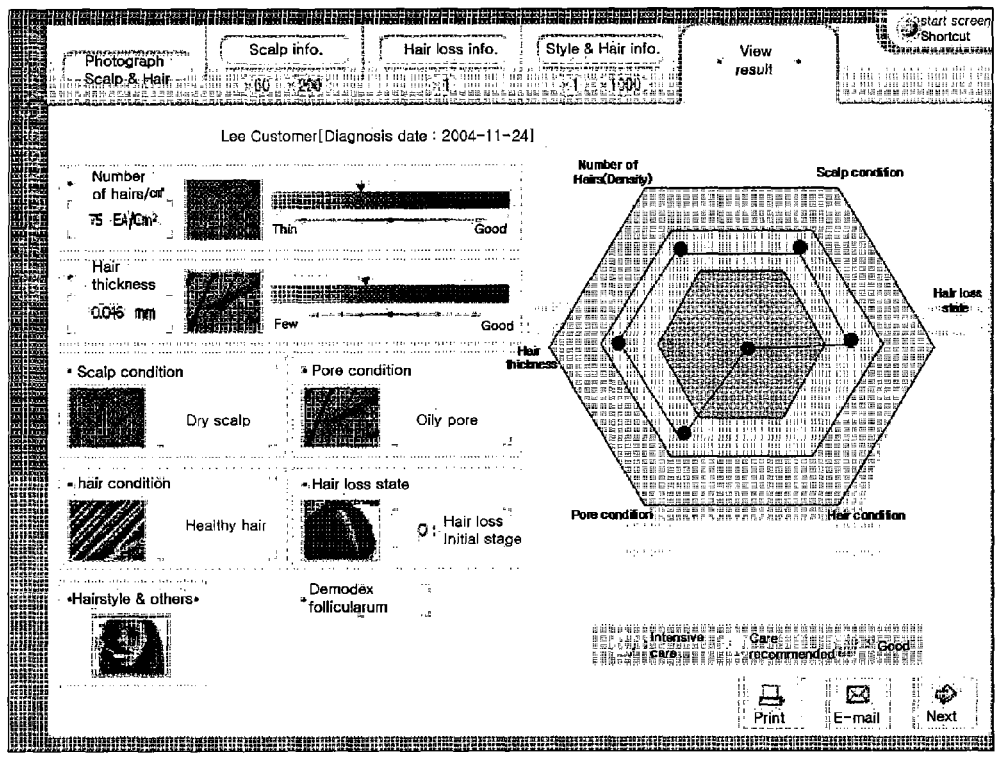
FIG. 9 is a monitor screen displaying a result of analyzing scalp and hair condition of a customer in the method of providing cosmetics customized for an individual customer according to the present invention.

FIG. 8 is a monitor screen displaying picture images obtained by photographing scalp and hair of a customer in the method of providing cosmetics customized for an individual customer according to the present invention, and FIG. 9 is a monitor screen displaying a result of analyzing scalp and hair condition of a customer in the method of providing cosmetics customized for an individual customer according to the present invention.

The step of diagnosing by interview may also be included in the step of measuring scalp and hair condition of a customer in the same manner as the step of measuring skin condition. In the step of diagnosing by interview, hereditary history of hair loss, a time where hair loss occurs, shampooing interval, degree of current stress, existence or not of demodex follicularum, details of disease, and the like of the customer are examined.

In order to measure the scalp and hair condition of the customer, picture images shown in FIG. 8 are first obtained by photographing the hairstyle, hair loss part, scalp, and hairs using different lenses coupled to the first camera of the diagnosis device depending on a corresponding measured item. Then, the scalp and hair condition of the customer, i.e., the number of hairs, hair thickness, scalp condition, pore condition, hair loss state, and hair condition, are measured from the obtained picture images referring to the manual of the device. In this step, the scalp and hair condition of the customer can be measured by comparing the picture image obtained through the first camera with a previously stored sample image and selecting either of them, or by counting the number of hairs or measuring thickness of a hair from the picture image.

Next, the measurement result of the scalp and hair of the customer is provided through a monitor screen as shown in FIG. 9 and transmitted to the microprocessor at the same time. The microprocessor analyzes the scalp and hair condition of the customer and calculates a material mixing ratio of hair care cosmetics appropriate for the scalp and hair condition of the customer on the basis of previously stored data.

The next steps are performed in the same manner as the steps of manufacturing and providing skin care cosmetics described above.

Figure 10:
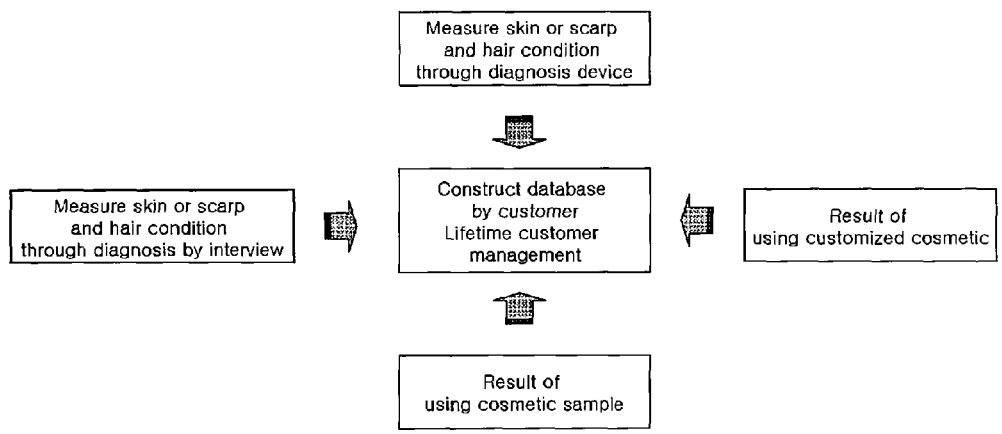
FIG. 10 is a view conceptually showing a process of constructing a database for an individual customer in the method of providing cosmetics customized for an individual customer according to the present invention.

FIG. 10 is a view conceptually showing a process of constructing a database for an individual customer in the method of providing cosmetics customized for an individual customer according to the present invention.

Referring to FIG. 10, it is shown that information obtained by measuring skin condition or scalp and hair condition of a customer using the diagnosis device, information obtained through a diagnosis by interview, information obtained from a result of using cosmetic samples, and information on skin condition or scalp and hair condition obtained by continuous use of customized cosmetics are collected and integrated to construct a database for each customer in order to provide customized cosmetics appropriate for skin condition or scalp and hair condition of each customer.

Customized cosmetics appropriate for skin condition or scalp and hair condition of a customer are produced utilizing such information, and therefore, demands of customers who desire cosmetics exactly appropriate for their own skin conditions, scalp and hair conditions, or tastes can be maximally fulfilled. In addition, such information is constructed as a database for each customer to thereby show changes in skin condition or scalp and hair condition of the customer, and the skin condition or scalp and hair condition of the customer can be easily managed using the database.

Although the present invention has been described and illustrated in connection with the specific preferred embodiments as described above, it will be readily understood that various modifications can be made thereto without departing from the scope of the present invention. Therefore, the scope of the present invention is not limited to the embodiments described above but is defined by the appended claims and the equivalents thereto.

INDUSTRIAL APPLICABILITY

In a method and system for providing cosmetics customized for an individual customer according to the present invention, skin condition or scalp and hair condition of the customer is measured and analyzed and then customized cosmetics appropriate for the features of the customer are produced and provided on the basis of the result of the analysis, whereby satisfaction of the customer can be maximized.

The invention claimed is:

1. A method for providing customized hair care cosmetics appropriate for an individual customer using a microprocessor having information on standard cosmetic material mixing ratios in accordance with scalp and hair conditions of consumers as a database, the method comprising the steps of:

measuring scalp and hair condition of a customer, including the number of hairs, hair thickness, hair condition, pore condition, and hair loss state of the customer, using a diagnosis device, wherein the diagnosis device includes a camera comprising a plurality of lenses having different magnification from one another to be selectively utilized, the specific lens utilized depending on the specific scalp and hair conditions of the customer being measured, the lens used to measure scalp conditions being different from the lens used to measure hair conditions, wherein a significantly higher magnification lens is used to measure hair conditions in comparison to the magnification of the lens used to measure scalp conditions;

comparing obtained images of scalp and hair conditions obtained by using the camera at selected magnifications to previously stored images to further measure and analyze scalp and hair conditions of a customer, said images of scalp conditions being different from the images of hair conditions and said images of the hair conditions being taken at a significantly higher magnification than the images of the scalp conditions;

diagnosing the customer by interview and receiving the result of the interview diagnosis including information selected from the group consisting of hereditary history of hair loss, a time where hair loss occurs, shampooing interval, degree of current stress, existence or not of demodex follicularum, and details of disease of the customer and utilizing the results of said interview diagnosis including information selected from the group consisting of hereditary history of hair loss, a time where hair loss occurs;

hampooing interval, degree of current stress, existence or not of demodex follicularum and details of disease of customer to diagnose and analyze scalp and hair condition of the customer;

calculating a cosmetic material mixing ratio appropriate for the customer through the microprocessor, on the basis of information on the measured scalp and hair condition of the customer using:

(i) the results of measuring the scalp condition obtained with the camera at a magnification appropriate for analyzing scalp conditions by comparing the images obtained by use of the camera with the previous stored images:

(ii) the results of measuring the hair condition obtained with the camera at a magnification appropriate for analyzing hair conditions by comparing the images obtained by use of the camera with the previous stored image, (iii) said images of the hair condition being different from the images of the scalp condition and in the images of the hair condition being at a significantly higher magnification than the images of the scalp condition, and (iv) the result of the diagnosis by interviewing the customer to ascertain information selected from the group consisting of hereditary history of hair loss, a time where hair loss occurs, shampooing interval, degree of current stress, existence or not of demodex follicularum, and details of disease of customer, and by adding or subtracting a mixing ratio of materials that need to be adjusted depending on the scalp and hair condition and the diagnosis results to or from a standard cosmetic material mixing ratio previously stored in the microprocessor in accordance with the scalp and hair condition; and manufacturing the customized hair care cosmetics using the calculated cosmetic material mixing ratio to provide the customer with the manufactured cosmetics.

2. A system for providing customized hair care cosmetics appropriate for an individual customer, the system comprising:

a diagnosis device configured to measure scalp and hair condition including the number of hairs, hair thickness, hair condition, pore condition, and hair loss state of a customer, the diagnosis device including a camera comprising a plurality of lenses having different magnifications from one another to be selectively utilized, the specific lens utilized depending on the specific scalp and hair condition of the customer being measured, the lens used to measure hair condition being different from the lens used to measure scalp condition and the lens used to measure hair condition being at a significantly higher magnification than the lens used to measure scalp condition;

a microprocessor having information on standard cosmetic material mixing ratios in accordance with scalp and hair conditions of consumers as a database, the microprocessor configured:

(a) to receive and utilize information on the scalp condition measured by the camera at a magnification appropriate to analyze the scalp condition by comparing the images of the scalp condition obtained using the camera at the appropriate magnification to measure scalp condition to images previously stored in the microcomputer, (b) to receive and utilize information on the hair condition measured by the camera at a magnification appropriate to analyze the hair condition by comparing the images of the hair condition obtained using the camera at the appropriate magnification to measure the hair condition to images previously stored in the microcomputer, (c) said images of the hair condition being different from the images of the scalp conditions and the images of the hair condition being at a magnification significantly higher than the magnification use to measure the scalp condition, as well as configured to receive and utilize information obtained from the customer selected from the group consisting of hereditary history of hair loss, the time when hair loss occurs, shampooing interval, degree of current stress, and existence or not of demodex follicularum of the customers for use in calculating a cosmetic material mixing ratio appropriate for the customer on the basis of the received information on the scalp and hair condition of the customer by adding or subtracting a mixing ratio of materials that need to be adjusted depending on the scalp and hair condition to or from a standard cosmetic material mixing ratio previously stored in the microprocessor in accordance with the scalp and hair condition; and a cosmetic manufacturing apparatus configured to receive the cosmetic material mixing ratio from the microprocessor and manufacturing the customized hair care cosmetics.

3. The method as claimed in claim 1, further comprising the step of, after the calculating step of the cosmetic material mixing ratio, manufacturing a cosmetic sample using the calculated cosmetic material mixing ratio, providing the customer with the manufactured cosmetic sample, and receiving a result of using the cosmetic sample from the customer.

4. The method as claimed in claim 1, further comprising the step of continuously collecting the information on the scalp and hair condition of the customer obtained in each of the aforementioned steps, accumulating the information on the scalp and hair condition of the customer in a database for the customers, and managing the accumulated information.

5. The system as claimed in claim 2, wherein the diagnosis device is connected to a user PC connected to a network, stores the information measured by the diagnosis device in the user PC, and transmits the measured information to the microprocessor through the network.

* * * * *

UNITED STATES PATENT AND TRADEMARK OFFICE
CERTIFICATE OF CORRECTION

| | |
|---|---|
| PATENT NO. | : 8,527,365 B2 |
| APPLICATION NO. | : 12/281843 |
| DATED | : September 3, 2013 |
| INVENTOR(S) | : D. S. Pak |

It is certified that error appears in the above-identified patent and that said Letters Patent is hereby corrected as shown below:

COLUMN     LINE

10        55    "hampooing" should read --shampooing--
(Claim 1,  line 38)

12        11    "use" should read --used--
(Claim 2,  line 36)

Signed and Sealed this
Third Day of November, 2015

Michelle K. Lee
*Director of the United States Patent and Trademark Office*